United States Patent
Iyer et al.

(10) Patent No.: US 9,714,416 B2
(45) Date of Patent: Jul. 25, 2017

(54) CELLULOLYTIC ENZYME COMPOSITIONS AND USES THEREOF

(71) Applicant: Novozymes A/S, Bagsvaerd (DK)

(72) Inventors: Prashant Iyer, Raleigh, NC (US); Armindo Ribiero Gaspar, Rolesville, NC (US); James Croonenberghs, Durham, NC (US); Thomas P. Binder, Decatur, IL (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/343,002

(22) PCT Filed: Sep. 21, 2012

(86) PCT No.: PCT/US2012/056502
§ 371 (c)(1),
(2) Date: Mar. 5, 2014

(87) PCT Pub. No.: WO2013/043981
PCT Pub. Date: Mar. 28, 2013

(65) Prior Publication Data
US 2014/0234915 A1 Aug. 21, 2014

Related U.S. Application Data

(60) Provisional application No. 61/538,211, filed on Sep. 23, 2011.

(51) Int. Cl.

| | | |
|---|---|---|
| C12P 19/14 | (2006.01) | |
| C12P 7/14 | (2006.01) | |
| C12N 9/18 | (2006.01) | |
| C07H 21/04 | (2006.01) | |
| C07K 1/00 | (2006.01) | |
| C12P 7/10 | (2006.01) | |
| C12N 9/42 | (2006.01) | |
| C12P 19/02 | (2006.01) | |
| C07K 14/37 | (2006.01) | |
| C12N 9/24 | (2006.01) | |

(52) U.S. Cl.
CPC ............... *C12N 9/18* (2013.01); *C07K 14/37* (2013.01); *C12N 9/2402* (2013.01); *C12N 9/2437* (2013.01); *C12N 9/2445* (2013.01); *C12P 7/10* (2013.01); *C12P 7/14* (2013.01); *C12P 19/02* (2013.01); *C12P 19/14* (2013.01); *C12Y 301/01072* (2013.01); *C12P 2203/00* (2013.01); *Y02E 50/16* (2013.01)

(58) Field of Classification Search
CPC ......... C12P 19/14; C12P 7/10; C12P 2203/00; C12P 7/14; C12P 19/02; C12Y 301/01072; Y02E 50/16; C07K 14/37; C12N 9/2402; C12N 9/2437; C12N 9/18; C12N 9/2445
USPC ........... 435/99, 162, 197; 536/23.2; 530/350
See application file for complete search history.

(56) References Cited

U.S. PATENT DOCUMENTS

| | | | |
|---|---|---|---|
| 8,034,996 B2* | 10/2011 | Lopez de Leon et al. ... | 800/288 |
| 2010/0031400 A1 | 2/2010 | Maranta et al. | |
| 2010/0043105 A1* | 2/2010 | Maranta et al. ............. | 800/298 |
| 2011/0111453 A1 | 5/2011 | McBrayer et al. | |

FOREIGN PATENT DOCUMENTS

| | | |
|---|---|---|
| WO | 2005/047499 A1 | 5/2005 |
| WO | 2006/078256 A2 | 7/2006 |
| WO | 2008/151079 A2 | 12/2008 |
| WO | 2009/042846 A1 | 4/2009 |
| WO | 2009/073709 A1 | 6/2009 |
| WO | 2009073709 A1 | 6/2009 |
| WO | 2010/108918 A1 | 9/2010 |
| WO | 2010/138754 A1 | 12/2010 |
| WO | 2011/041397 A1 | 4/2011 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Frisoni et al., Natural Cellulose Fibers: Heterogeneous acetylation kinetics and biodegradation behavior. Biomacromolecules, 2001, vol. 2: 476-482.*
Selig et al., The impact of cell wall acetylation on corn stover hydrolysis by cellulolytic and xyanolytic enzymes. Cellulose, 2009, vol. 16: 711-722.*
Altaner et al., Specificity of an Aspergillus niger esterase deacetylating cellulose acetate. Cellulose, 2003, vol. 10: 85-95.*
Moriyoshi et al., Purification and characterization of an esterase involved in cellulose acetate degradation by *Neisseria sicca* SB. Biosci. Biotechnol. Biochem., 1999, vol. 63 (10): 1708-1713.*
Puls et al., 4.3 Degradation and modification of cellulose acetates by biological systems. Macromol. Symp. 2004, vol. 208: 239-253.*
Sluiter et al., Determination of structural carbohydrates and lignin biomass: Laboratory Analytical Procedure (LAP: NREL/TP-501-4268, Jul. 2011: 18 pages total.*
Biswas et al., Process for obtaining cellulose acetate from agricultural by-products. Carbohyd. Polymers., 2006, vol. 64: 134-137.*
Sassi et al., Ultrastructural aspects of the acetylation of cellulose. Cellulose, 1995, vol. 2: 111-127.*
Selig et al, 2009, Cell, vol. 16, pp. 711-722.
Altaner et al, Cellulose 00, 1-7 (2002).
Christov et al, Enzyme Microb Technol, vol. 15, No. 6, pp. 460-475 (1993).
Khan et al, Mircen J, vol. 5, pp. 49-54 (1989).
Zhang et al, Biotechnol Biofuels, vol. 4, No. 1, Article 60 (2011).

* cited by examiner

*Primary Examiner* — Ganapathirama Raghu
(74) *Attorney, Agent, or Firm* — Kelly Reynolds

(57) ABSTRACT

The present invention relates enzyme composition comprising a cellulolytic preparation and an acetylxylan esterase (AXE); and the used of cellulolytic enzyme compositions for hydrolyzing acetylated cellulosic material. Finally the invention also relates to processes of producing fermentation products from acetylated cellulosic materials using a cellulolytic enzyme composition of the invention.

24 Claims, 3 Drawing Sheets

SEQUENCE LISTING

```
<160> NUMBER OF SEQ ID NOS: 3

<210> SEQ ID NO 1
<211> LENGTH: 413
<212> TYPE: PRT
<213> ORGANISM: Thielavia terrestris

<400> SEQUENCE: 1

Met Lys Pro Ser Val Val Ala Gly Leu Phe Ala Ser Gly Ala Ala Ala
1               5                   10                  15

Gln Ser Gly Ala Trp Gly Gln Cys Gly Gly Ile Gly Tyr Thr Gly Pro
            20                  25                  30

Thr Ser Cys Val Ser Gly Tyr Arg Cys Val Tyr Val Asn Asp Trp Tyr
        35                  40                  45

Ser Gln Cys Gln Pro Gly Ala Ala Thr Thr Thr Ser Pro Pro Ala
    50                  55                  60
```

```
Ser Ser Thr Ser Thr Pro Pro Thr Ser Thr Gly Thr Ala Gly Val Arg
 65                  70                  75                  80

Tyr Val Gly Arg Val Asn Pro Ser Thr Lys Glu Leu Ser Trp Pro Gly
                 85                  90                  95

Thr Gly Ile Ser Phe Thr Phe Thr Gly Thr Ser Ala Thr Ile Gly Ile
            100                 105                 110

Ala Ser Val Ser Gly Thr Asn Ser Val Asp Leu Val Asp Asp Gly
        115                 120                 125

Asp Pro Ile Val Ile Thr Ser Phe Gly Ser Ser Ile Thr Thr Pro Ala
130                 135                 140

Gly Leu Ser Gln Gly Thr His Thr Val Thr Leu Arg Lys Arg Ser Glu
145                 150                 155                 160

Ala Leu Tyr Gly Ser Ile Phe Leu Gly Ser Val Thr Thr Asp Gly Ala
                165                 170                 175

Phe Val Ala Gly Thr Val Pro Thr Arg Gln Ile Glu Ile Ile Gly Asp
            180                 185                 190

Ser Ile Thr Val Gly Tyr Gly Leu Asp Gly Thr Asn Pro Cys Thr Asn
        195                 200                 205

Asn Ala Thr Val Glu Asp Asn Pro Lys Thr Tyr Gly Ala Leu Ala Ala
210                 215                 220

Ala Ala Leu Gly Ala Asp Tyr Asn Val Ile Ala Trp Ser Gly Lys Gly
225                 230                 235                 240

Val Val Arg Asn Val Ala Thr Gly Ser Pro Asp Thr Ser Pro Leu Met
                245                 250                 255

Pro Glu Leu Tyr Thr Arg Tyr Gly Ala Asn Asp Pro Asn Ser Tyr
            260                 265                 270

Pro Tyr Pro Pro Thr Trp Ser Pro Asp Ala Val Val Ile Asn Leu Gly
        275                 280                 285

Thr Asn Asp Phe Ser Tyr Ile Ala Trp Asp Ala Ser Gly Asn Ala Tyr
290                 295                 300

Ala Ala Arg Pro Pro Leu Asn Ala Thr Thr Tyr Thr Asp Gly Met Val
305                 310                 315                 320

Ala Phe Ala Gln Ser Ile Arg Ala His Tyr Pro Ala Ala His Val Phe
                325                 330                 335

Leu Val Gly Ser Pro Met Leu Ser Asp Ser Tyr Pro Thr Ala Ala Asp
            340                 345                 350

Ala Gln Lys Thr Thr Gln Thr Asn Ala Leu Lys Ser Ala Val Ala Gln
        355                 360                 365

Leu Gly Ala Asn Ala His Phe Val Asp Trp Ser Thr Gln Gly Ser Asp
370                 375                 380

Val Gly Cys Asp Tyr His Pro Asn Ala Ala Thr His Ala Ala Glu Ala
385                 390                 395                 400

Ala Val Leu Ala Asp Ala Ile Arg Ser Ala Leu Gly Trp
                405                 410

<210> SEQ ID NO 2
<211> LENGTH: 291
<212> TYPE: PRT
<213> ORGANISM: Aspergillus aculeatus

<400> SEQUENCE: 2

Met Lys Thr Leu Phe Gly Phe Ala Gly Ala Ser Leu Ala Leu Ala Trp
 1               5                  10                  15

Ser Ala Ala Ala Thr Thr Lys Tyr Val Ile Ser Phe Gly Asp Ser Tyr
                20                  25                  30
```

```
Thr Ser Thr Thr Phe Asn Ile Thr Gly Thr Lys Pro Ser Ala Ala Asn
         35                  40                  45

Pro Leu Gly Asn Pro Pro Tyr Pro Gly Trp Thr Ala Ser Gly Gly Thr
 50                  55                  60

Asn Trp Ile Ser Asp Ile Val Ala Lys Tyr Asn Asn Ser Leu Leu Leu
 65                  70                  75                  80

Ser Tyr Asn Leu Ala Tyr Gly Gly Ala Thr Val Asn Ala Ser Leu Val
                 85                  90                  95

Ala Pro Tyr Leu Pro Thr Val Tyr Ser Ile Ile Asp Gln Val Asp Glu
             100                 105                 110

Phe Gln Glu Tyr Leu Ser Pro Pro Ser Trp Ala Pro Trp Asp Ala
             115                 120                 125

Lys Asn Thr Leu Phe Ala Val Trp Ile Gly Val Asn Asp Val Ala Gly
         130                 135                 140

Ser Trp Tyr Gln Thr Ser Ala Ala Leu Glu Arg Glu Ile Leu Asp
145                 150                 155                 160

Gln Leu Phe Glu Gln Ile Glu His Val Tyr Gln Gly Gly Ala Arg Asn
                 165                 170                 175

Phe Ala Leu Leu Thr Val Pro Pro Ile Glu Arg Thr Pro Asn Ile Met
             180                 185                 190

Gln Gly Ser Asp Pro Asp Tyr Thr Ile Pro Arg Leu Lys Ala Ala Ile
         195                 200                 205

Glu His Trp Asn Thr Ile Leu Val Glu Lys Ala Glu Ala Leu Ala Gln
210                 215                 220

Thr His His Asp Ala Ile Val Lys Val Val Asp Thr Gln Pro Val Phe
225                 230                 235                 240

Asn Asn Ile Leu Asp Ser Gly Gly Ala Ala Ala Asp Cys Trp Asn Ser
                 245                 250                 255

Asp Gly Val Thr Cys Leu Trp Phe Asn Asp Phe His Pro Gly Ile Val
             260                 265                 270

Ile Gln Asp Ala Val Ala Gln Ala Val Ala Ala Trp Lys Gly Ser
         275                 280                 285

Phe Phe Thr
    290

<210> SEQ ID NO 3
<211> LENGTH: 377
<212> TYPE: PRT
<213> ORGANISM: Humicola insolens

<400> SEQUENCE: 3

Met Lys Val Pro Thr Leu Ile Ser Ser Leu Leu Ala Leu Val Ser Phe
1               5                  10                  15

Ser Glu Ala Thr Pro Leu Ile Lys Arg Ala Thr Leu Thr Arg Val Asn
             20                  25                  30

Asn Phe Gly Asn Asn Pro Ser Gly Ala Arg Met Tyr Ile Tyr Val Pro
         35                  40                  45

Asp Arg Leu Gln Pro Arg Pro Ala Val Leu Thr Ala Val His Tyr Cys
     50                  55                  60

Thr Gly Thr Ala Asn Ala Phe Tyr Thr Gly Thr Pro Tyr Ala Arg Leu
65                  70                  75                  80

Ala Asp Gln Tyr Gly Phe Ile Val Val Tyr Pro Glu Ser Pro Asn Asn
                 85                  90                  95

Gly Gly Cys Trp Asp Val Ser Ser Arg Ala Ala Tyr Thr Arg Asp Ser
             100                 105                 110
```

```
Gly Ser Asn Ser His Ala Ile Ser Leu Met Thr Lys Trp Ala Leu Gln
            115                 120                 125

Gln Tyr Asn Gly Asp Pro Glu Lys Val Phe Val Ala Gly Thr Ser Ser
            130                 135                 140

Gly Ala Met Met Thr Asn Val Leu Ser Ala Val Tyr Pro Asp Leu Tyr
145                 150                 155                 160

Lys Ala Ala Ala Ala Tyr Ala Gly Val Pro Ala Gly Cys Phe Tyr Thr
                165                 170                 175

Gly Thr Val Ala Gly Trp Asn Ser Thr Cys Ala Asn Gly Gln Ser Ile
                180                 185                 190

Thr Thr Gln Glu His Trp Ala Arg Thr Ala Leu Asp Met Tyr Pro Gly
            195                 200                 205

Tyr Thr Gly Pro Arg Pro Arg Met Leu Ile Tyr His Gly Ser Ala Asp
            210                 215                 220

Thr Thr Ile Tyr Pro Arg Asn Phe Asn Glu Thr Leu Lys Gln Trp Ala
225                 230                 235                 240

Gly Val Phe Gly Tyr Thr Tyr Gly Gln Pro Gln Gln Thr Leu Pro Asn
                245                 250                 255

Thr Pro Ser Ala Pro Tyr Thr Lys Tyr Val Tyr Gly Pro Asn Leu Val
                260                 265                 270

Gly Ile Tyr Gly Ser Gly Val Thr His Asn Ile Pro Val Asn Gly Ala
                275                 280                 285

Asn Asp Met Glu Trp Phe Gly Ile Thr Gly Asn Pro Thr Thr Thr Ser
            290                 295                 300

Thr Ser Ala Thr Val Pro Thr Thr Thr Ser Ser Pro Gly Thr Thr Ser
305                 310                 315                 320

Thr Ser Ala Pro Val Thr Thr Thr Thr Ser Arg Ala Pro Pro Pro Pro
                325                 330                 335

Thr Gln Thr Cys Ile Pro Val Pro Arg Trp Gly Gln Cys Gly Gly Ile
            340                 345                 350

Thr Trp Gly Gly Cys Thr Val Cys Glu Ala Pro Tyr Thr Cys Gln Lys
            355                 360                 365

Leu Asn Asp Trp Tyr Ser Gln Cys Leu
370                 375
```

CELLULOLYTIC ENZYME COMPOSITIONS AND USES THEREOF

CROSS-REFERENCE TO RELATED APPLICATIONS

This application is a 35 U.S.C. 371 National Application of PCT/US2012/056502 filed Sep. 21, 2012 which claims priority or the benefit under 35 U.S.C. 119 of U.S. Provisional Patent Application No. 61/538,211 filed Sep. 23, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Department of Energy Grant No: DE-EE0002870. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to cellulolytic enzyme compositions; methods of using such cellulolytic composition for hydrolyzing acetylated cellulosic materials; and processes of producing fermentation products using cellulolytic enzyme compositions of the invention.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

The rate and extent of enzymatic hydrolysis of cellulosic material depends on various structural features such lignin content, acetyl content and crystallinity. In native plants hemicellulosic material, such as xylan, has some degree of natural acetylation, while cellulosic material (cellulose) does not. However, when cellulosic material is subjected to pretreatment with, e.g., acids, such as acetic acid, acetylation occurs. Such acetylation of cellulosic material impacts enzymatic digestibility.

WO 2005/047499 discloses an *Aspergillus fumigatus* beta-glucosidase and gene thereof.

WO 2006/078256 discloses *Aspergillus fumigatus* GH10 xylanases.

WO 2008/151079 discloses compositions for degrading cellulose material.

WO 2009/042846 disclosed an acetylxylan esterase (AXE) derived from *Thielavia terrestris*.

WO 2011/041397 discloses a *Penicillium* sp. GH61 polypeptide having cellulolytic enhancing activity and gene thereof.

WO 2011/057140 discloses an *Aspergillus fumigatus* cellobiohydrolase I; *Aspergillus fumigatus* cellobiohydrolase II; and an *Aspergillus fumigatus* beta-xylosidase.

There is a need for cellulolytic enzyme compositions that can hydrolyze acetylated cellulosic materials more efficiently.

SUMMARY OF THE INVENTION

The present invention relates to enzyme compositions comprising cellulolytic activity; the use thereof for hydrolyzing acetylated cellulosic materials; and processes of producing fermentation products using a cellulolytic enzyme composition of the invention.

In the first aspect the invention relates to an enzyme composition comprising a cellulolytic preparation and an acetylxylan esterase (AXE).

In the second aspect the invention relates to methods of hydrolyzing acetylated cellulosic material, comprising subjecting the acetylated cellulosic material to an enzyme composition of the invention comprising a cellulolytic preparation and an acetylxylan esterase (AXE).

In an embodiment the acetylxylan esterase (AXE) is derived from a strain of the genus *Thielavia*, such as a strain of *Thielavia terrestris*, such as one disclosed in WO 2009/042846 as SEQ ID NO: 2 or SEQ ID NO: 1 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2009/042846 or SEQ ID NO: 1 herein.

In the third aspect the invention relates to processes of producing a fermentation product from acetylated cellulosic material, comprising:

(a) hydrolyzing said acetylated cellulosic material by subjecting the material to an enzyme composition of the invention or according to the hydrolysis method of the invention;

(b) fermenting using a fermenting organism; and (c) optionally recovering the fermentation product.

Definitions

Figure 1:
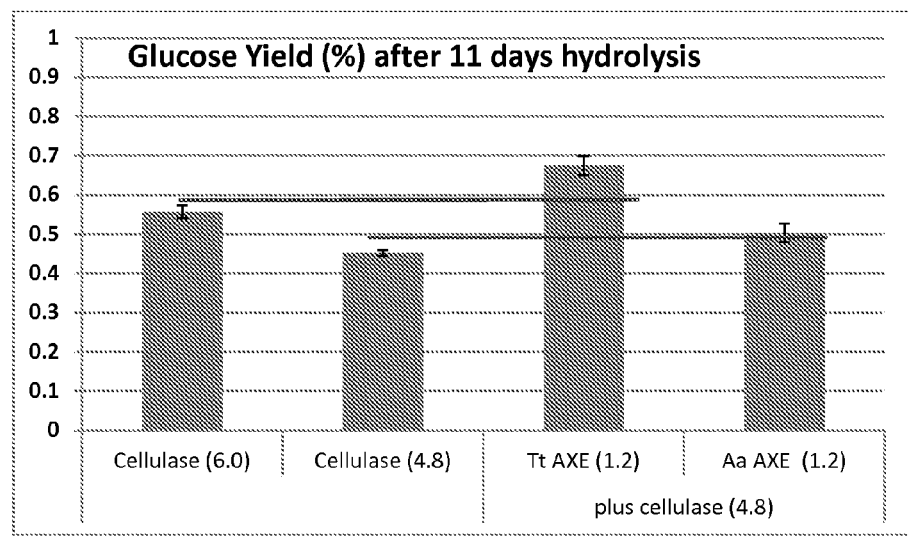
FIG. 1 shows the glucose yield (%) after 11 days hydrolysis.

Acetylated Cellulosic material: The term "acetylated cellulosic material" refers to cellulosic material that has a higher degree of acetylation than native cellulosic material. In an embodiment the acetylation-% for the target cellulosic substrate may be as high as 30% (average acetyl groups per sugar units). In an embodiment the acetylated cellulosic material is 0.1-30%, such as 0.5-20%, preferably 1-10%, such as around 5-10%, such as around 8% acetylated. Acetylation can be determined according to the NREL procedures described in Technical Report NREL/TP-510-42618 (Revised July 2011) and as described in the "Materials & Methods" section.

Cellulosic material: The term "cellulosic material" means any material containing cellulose. The predominant polysaccharide in the primary cell wall of cellulosic material is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No1 filter paper as the substrate. The assay was established by the International Union of Pure and Applied Chemistry (IUPAC) (chose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of cellulose when used in conjunction with a cellulase or a mixture of cellulases.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5 (Novozymes NS, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Variant: The term "variant" means a polypeptide having enzyme activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

The present invention relates to cellulolytic enzyme compositions; the use thereof for hydrolyzing acetylated cellulosic material; and processes of producing fermentation products using a cellulolytic enzyme composition of the invention.

The inventors have found that enzyme compositions comprising cellulolytic preparations boost conversion of acetylated cellulosic material. More specifically the inventors surprisingly found that when including acetylxylan esterases (AXEs), in particular acetylxylan esterase derived from *Thilavia terrestris*, in cellulolytic preparations the cellulose conversion of pretreated acetylated cellulosic material is boosted. For instance, Example 1 shows that acetylxylan esterases (AXEs) boost the glucose and xylose yield when used for cellulolytic hydrolysis of pretreated acetylated corn stover pulp compared to hydrolysis with cellulolytic compositions, but without an acetylxylan esterase (AXE).

Enzyme Compositions of the Invention

In the first aspect the invention relates to an enzyme composition comprising a cellulolytic preparation and an acetylxylan esterase (AXE).

In an embodiment the cellulolytic preparation is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic preparation is derived from a strain of *Trichoderma reesei*.

Cellulolytic Preparation

The cellulolytic preparation may comprise one or more of the following polypeptides, such as enzymes: GH61 polypeptide having cellulolytic enhancing activity, beta-glucosidase, xylanase, beta-xylosidase, CBHI, CBHII, or a mixture of two, three, four, five or six thereof.

In an embodiment the cellulolytic preparation comprises a GH61 polypeptide having cellulolytic enhancing activity and a beta-glucosidase.

In another embodiment the cellulolytic preparation comprises a GH61 polypeptide having cellulolytic enhancing activity, a beta-glucosidase, and a xylanase.

In another embodiment the cellulolytic preparation comprises a GH61 polypeptide having cellulolytic enhancing activity, a beta-glucosidase, a xylanase and a beta-xylosidase.

In another embodiment the cellulolytic preparation comprises a GH61 polypeptide having cellulolytic enhancing activity, a beta-glucosidase, a xylanase, a beta-xylosidase, and a CBHI.

In another embodiment the cellulolytic preparation comprises a GH61 polypeptide having cellulolytic enhancing activity, a beta-glucosidase, a xylanase, a beta-xylosidase, a CBHI and a CBHII.

Other enzymes, such as endoglucanases, may also be comprises in the cellulolytic preparation.

Beta-Glucosidase

The cellulolytic preparation may in one embodiment comprise one or more beta-glucosidase. The beta-glucosidase may in one embodiment be one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigates*, such as such as one disclosed in WO 2005/047499 or an *Aspergillus fumigatus* beta-glucosidase variant In an embodiment a beta-glucosidase may also be present or added during hydrolysis. The beta-glucosidase may be an *Aspergillus fumigatus* beta-glucosidase (e.g., SEQ ID NO: 2 of WO 2005/047499) or a variant thereof disclosed in WO 2012/044915 (hereby incorporated by reference), such as one with the following substitutions: F100D, S283G, N456E, F512Y In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

GH61 Polypeptide Having Cellulolytic Enhancing Activity

The cellulolytic preparation may in one embodiment comprise one or more GH61 polypeptide having cellulolytic enhancing activity. In one embodiment the enzyme composition comprises a GH61 polypeptide having cellulolytic enhancing activity, such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigates*, such as the one described in WO 2010/138754 as SEQ ID NO: 2; or one derived from a strain derived from *Penicillium*, such as a strain of *Penicillium emersonii*, such as the one disclosed in WO 2011/041397.

Xylanase

The cellulolytic preparation may in one embodiment comprise one or more xylanase. In one embodiment the cellulolytic preparation comprises an xylanase, preferably a GH10 xylanase, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

Beta-xylosidase

The cellulolytic preparation may in one embodiment comprise one or more beta-xylosidase. In one embodiment the cellulolytic preparation comprises a beta-xylosidase, such as one derived from a strain of the genus *Aspergillus*, such as a strain of *Aspergillus fumigatus*, such as the one disclosed in co-pending U.S. provisional No. 61/526,833 or PCT/US12/052163 (Examples 16 and 17), or derived from a strain of *Trichoderma*, such as a strain of *Trichoderma reesei*, such as the mature polypeptide of SEQ ID NO: 58 in WO 2011/057140.

CBH I

The cellulolytic preparation may in one embodiment comprise one or more CBH I (cellobiohydrolase I). In one embodiment the cellulolytic preparation comprises a cellobiohydrolase I (CBHI), such as one derived from a strain of the genus *Aspergillus*, such as a strain of *Aspergillus fumigatus*, such as the Cel7A CBHI disclosed in SEQ ID NO: 2 in WO 2011/057140, or a strain of the genus *Trichoderma*, such as a strain of *Trichoderma reesei*.

CBH II

The cellulolytic preparation may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

Acetylxylan Esterase (AXE)

The enzyme composition comprises beside the cellulolytic preparation also an acetylxylan esterase (AXE). In an embodiment the acetylxylan esterase (AXE) is derived from a strain of the genus *Thielavia*, such as a strain of *Thielavia terrestris*, such as one disclosed in WO 2009/042846 as SEQ ID NO: 2 or SEQ ID NO: 1 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2009/042846 or SEQ ID NO: 1 herein.

In another embodiment the acetylxylan esterase (AXE) is derived from a strain of the genus *Aspergillus*, such as a strain of *Aspergillus aculaetus*, such as one disclosed in WO 2010/108918 as SEQ ID NO: 2, or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2010/108918.

In another embodiment the acetylxylan esterase (AXE) is derived from a strain of the genus *Aspergillus*, such as a strain of *Aspergillus aculaetus*, such as *Aspergillus aculeatus* CBS 101.43, such as the one disclosed in WO 95/02689 as SEQ ID NO: 5 or an acetylxylan esterase having at least 80%, such as at least 85%, such as at least 90%, preferably 95%, such as at least 96%, such as 97%, such as at least 98%, such as at least 99% identity to SEQ ID NO: 5 in WO 95/02689.

In an embodiment the acetylxylan esterase (AXE) is derived from a strain of the genus *Humicola*, such as a strain of *Humicola insolens*, such as one disclosed in WO 2009/073709 as SEQ ID NO: 2 or as SEQ ID NO: 3 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2009/073709 or as SEQ ID NO: 3 herein.

In an embodiment the acetylxylan esterase (AXE) is derived from a strain of the genus *Aspergillus*, such as a strain of *Aspergillus aculaetus*, such as one disclosed in WO 2010/108918 as SEQ ID NO: 2 or as SEQ ID NO: 2 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2010/108918 or as SEQ ID NO: 2 herein.

In a preferred embodiment the acetylxylan esterase is derived from is derived from a strain of the genus *Thielavia*, more preferred a strain of *Thielavia terrestris*, even more preferred the one disclosed in WO 2009/042846 as SEQ ID NO: 2 or SEQ ID NO: 1 herein.

Cellulolytic Preparations

As mentioned above the cellulolytic preparation may comprise a number of difference polypeptides, such as enzymes.

In an embodiment the cellulolytic preparation comprises a *Trichoderma reesei* cellulolytic preparation, further comprising *Thermoascus aurantiacus* GH61A polypeptide having cellulolytic enhancing activity (WO 2005/074656), *Aspergillus oryzae* beta-glucosidase fusion protein (WO 2008/057637), and *Aspergillus aculeatus* xylanase (Xyl II in WO 94/21785).

In another embodiment the cellulolytic preparation comprises a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785).

In another embodiment the cellulolytic preparation comprises a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785) and the acetylxylan esterase (AXE) is the one derived from *Thielavia terrestris* disclosed in WO 2009/042846 as SEQ ID NO: 2 or SEQ ID NO: 1 herein or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846 or SEQ ID NO: 1 herein.

In another embodiment the cellulolytic preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) and *Aspergillus fumigatus* xylanase (Xyl III in WO 2006/078256) and the acetylxylan esterase (AXE) is the one derived from *Thielavia terrestris* disclosed in WO 2009/042846 as SEQ ID NO: 2 or SEQ ID NO: 1 herein or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846 or SEQ ID NO: 1 herein.

The enzyme composition of the present invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes. The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Ratio Between Cellulolytic Preparation and Acetylxylan Esterase (AXE)

According to the invention the acetylxylan esterase and cellulolytic preparation is mixed in a ratio that results in improved hydrolysis of the acetylated lignocellulolytic material.

The optimum amount of acetylxylan esterase depends on several factors including, but not limited to, the mixture of component cellulolytic and/or hemicellulolytic enzymes, the acetylated cellulosic material, the concentration of acetylated cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic preparation added to the acetylated cellulosic material is about 0.01 to about 50.0 mg, e.g., about 1 to about 25 mg, such as about 2 to about 10 mg, such as about 4 to about 8 mg protein per g/DS of the cellulosic material.

In an embodiment the acetylxylan esterase (AXE) is used in an amount of, e.g., 0.01 to about 10 mg, such as 0.05 to about 5 mg, such as 0.1 to about 4 mg enzyme protein per DS of the cellulosic material.

In an embodiment the ratio between cellulolytic preparation and acetylxylan esterase (AXE) is in the range between 500:1 and 1:1, such as between 50:1 and 2:1, such as around 4:1.

In a preferred embodiment the cellulolytic preparation is derived from *Trichoderma reesei* and the acetylxylan esterase is derived from a strain of the genus *Thielavia*, such as a strain of *Thielavia terrestris*, such as the one disclosed in WO 2009/042846 as SEQ ID NO: 2 or SEQ ID NO: 1 herein or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846 or SEQ ID NO: 1 herein, in a ratio of between 500:1 and 1:1, such as between 50:1 and 2:1, such as about 4:1.

Hydrolysis Methods of the Invention

Cellulosic material is not natively acetylated. However, when cellulosic materials are subjected to pretreatment with, e.g., acids, such as acetic acid, acetylation occurs. Such acetylation impacts enzymatic digestibility of the cellulosic material during hydrolysis. During hydrolysis, also known as saccharification, the acetylated cellulosic material is hydrolyzed to break down cellulose and/or hemicellulose to fermentable sugars, such as glucose, cellobiose, xylose, xylulose, arabinose, mannose, galactose, and/or soluble oligosaccharides. Hydrolysis may according to the invention be performed enzymatically using an enzyme composition of the present invention.

In the second aspect the invention relates to methods of hydrolyzing acetylated cellulosic material comprising subjecting the acetylated cellulosic material to a cellulolytic preparation and an acetylxylan esterase (AXE). In an embodiment the acetylated cellulosic material is pretreated cellulosic material.

Acetylated Cellulosic Materials

Acetylated cellulosic material refers to cellulosic material that has a higher degree of acetylation than native cellulosic material. The acetylated cellulosic material may be plant material that comprises cellulosic material (defined above). Usually the acetylated cellulosic material also comprises hemicellulosic material, such as xylans, xyloglucans, arabinoxylans, and mannans in complex branched structures with a spectrum of substituents.

In an embodiment the acetylated cellulosic material is plant material chips, plant stem segments and/or whole plant stems. In an embodiment the cellulosic material is selected from the group consisting of arundo, bagasse, bamboo, corn cob, corn fiber, corn stover, miscanthus, orange peel, rice straw, switchgrass, wheat straw. In a preferred embodiment the source of the cellulosic material is corn stover, corn cobs, and/or wheat straw. In a preferred embodiment the acetylated cellulosic material is acetylated corn stover pulp.

Pretreatment

The cellulosic material can be subjected to particle size reduction, sieving, pre-soaking, wetting, washing, and/or conditioning before pretreatment using methods known in the art.

The cellulosic material may have been subjected to conventional pretreatments. Conventional pretreatments include, but are not limited to, steam pretreatment (with or without explosion), acid pretreatment, such as dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments. Acid pretreatment is preferred.

The cellulosic material is preferably pretreated before hydrolysis. Alternatively, the pretreatment can be carried out simultaneously with enzyme hydrolysis to release fermentable sugars, such as glucose, xylose, and/or cellobiose.

The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, acid pretreatment, such as dilute acid pretreatment, lime pretreatment, wet oxidation, ammonia fiber/freeze explosion (AFEX), ammonia percolation (APR), ionic liquid, and organosolv pretreatments. Pretreatments including acid pretreatment is preferred.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

In one aspect, the chemical pretreatment is preferably carried out as acid pretreatment, such as dilute acid treatment, such as a continuous dilute acid treatment.

The acid is preferably carried out using acetic acid. However, other acid such as sulfuric acid, citric acid, nitric acid, phosphoric acid, tartaric acid, succinic acid, hydrogen chloride, or mixtures thereof, can also be used.

Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt % acid. The acid is contacted with the cellulosic material and held at a temperature, e.g., in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt. %, e.g., 20-70 wt. % or 30-60 wt. %, such as around 40 wt. %. The pretreated cellulosic material can be unwashed or washed using any method known in the art, e.g., washed with water.

The terms "mechanical pretreatment" or "physical pretreatment" refer to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can, e.g., be coupled with steaming/steam explosion, hydrothermolysis, acid pretreatment, such as dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating Lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241;

Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Preferred pretreatments include chemical pretreatment, a physical pretreatment, or a chemical pretreatment and a physical pretreatment. In an embodiment the cellulosic material is subjected to thermomechanically pulping. In an embodiment the acetylated cellulosic material has been thermomechanically pulped.

In an embodiment the acetylated cellulosic material is prepared by pretreatment, includes acid pretreatment.

In an embodiment the acetylated cellulosic material has been prepared by pretreating cellulosic material at high temperature, high pressure and/or acid pretreatment.

In an embodiment the acid pretreatment is done using acetic acid, or another acid.

In an embodiment the acetylated cellulosic material has been prepared by pretreating cellulosic material using organosolv pretreatement, such as Acetosolv and Acetocell processes.

In an embodiment the soluble fractions containing sugars, acid(s) and solubilized lignin is removed from the acetylated cellulosic material after pretreatment.

In an embodiment hydrolysis of the acetylated cellulosic material is carried out at a temperature between 20-70° C., such as 30-60° C., preferably 45-55° C. at a pH in the range 4-6, such as 4.5-5.5. The acetylated cellulosic material may in an embodiment be present at 1-20 (w/w) % of TS, such as 2-10 (w/w) % TS (Total Solids), such as around 5 (w/w) % TS.

In an embodiment the hydrolysis is carried out for 1-20 days, preferably 5-15 days.

According to the invention hydrolysis is carried out using an enzyme composition of the invention comprising a cellulolytic preparation and an acetylxylan esterase (AXE) as defined in the "Enzyme Composition of the Invention"-section above.

Hydrolysis is carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the acetylated cellulosic material is fed gradually to, for example, an enzyme composition containing hydrolysis solution.

The hydrolysis (i.e., saccharification) is generally performed in stirred-tank reactors or fermentors under controlled pH, temperature, and mixing conditions. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt. %, e.g., about 10 to about 40 wt. % or about 20 to about 30 wt. %.

Process of Producing Fermentation Products From Acetylated Cellulosic Material

In a third aspect the invention is directed to processes of using an enzyme composition of the present invention.

In a preferred embodiment the invention relates to processes of producing a fermentation product from acetylated cellulosic material, comprising:

(a) hydrolyzing said acetylated cellulosic material by subjecting the material to an enzyme composition of the invention or according to a hydrolysis method of the invention;

(b) fermenting using a fermenting organism; and (c) optionally recovering the fermentation product.

According to the process of the invention hydrolysis (i.e., saccharification) and fermentation may be carried out separate or simultaneous. In an embodiment the process of the invention is carried out as separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); or direct microbial conversion (DMC), also sometimes called consolidated bioprocessing (CBP). SHF uses separate process steps to first enzymatically hydrolyze the acetylated cellulosic material to fermentable sugars, e.g., glucose, cellobiose, and pentose monomers, and then ferment the fermentable sugars to ethanol. In SSF, the enzymatic hydrolysis of the acetylated cellulosic material and the fermentation of sugars to ethanol are combined in one step. SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic hydrolysis (saccharification) followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product.

The acetylated cellulosic material may be a material as described in the "Acetylated Cellulosic Materials" section. Hydrolysis is carried in accordance with the "Hydrolysis Methods of the Invention" section.

Fermentation

The fermentable sugars obtained from the hydrolyzed acetylated cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Fermenting Microorganism

The term "fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophilia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

According to the invention the term "fermentation product" can be any substance derived from fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more (e.g., several) hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, Miya, and Kiriyama, 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy*, 13(1-2): 83-114.

In another preferred aspect, the fermentation product is isoprene.

In another preferred aspect, the fermentation product is a ketone. It will be understood that the term "ketone" encompasses a substance that contains one or more (e.g., several) ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

Recovery

The fermentation product(s) are optionally recovered after fermentation using any method known in the art including, but not limited to, chromatography, electrophoretic procedures, differential solubility, distillation, or extraction. For example, alcohol, such as ethanol, is separated from the fermented material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

The invention is further defined by the following paragraphs:

Paragraph 1. An enzyme composition comprising a cellulolytic preparation and an acetylxylan esterase (AXE).

Paragraph 2. The enzyme composition of paragraph 1, wherein the cellulolytic preparation is derived from *Trichoderma reesei, Humicola insolens* or *Chrysosporium lucknowense*.

Paragraph 3. The enzyme composition of paragraph 1 or 2, wherein the cellulolytic preparation comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigates*, such as such as one disclosed in WO 2005/047499 or an *Aspergillus fumigatus* beta-glucosidase variant disclosed in co-pending U.S. provisional application No. 61/388,997 or WO 2012/044915 with the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

Paragraph 4. The enzyme composition of any of paragraphs 1-3, wherein the cellulolytic preparation comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigates*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397.

Paragraph 5. The enzyme composition of any of paragraphs 1-4, wherein the cellulolytic preparation comprises a xylanase, preferably a GH10 xylanase, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

Paragraph 6. The enzyme composition of any of paragraphs 1-5, wherein the cellulolytic preparation comprises a beta-xylosidase, such as one derived from a strain of the genus *Aspergillus*, such as a strain of *Aspergillus fumigatus*, such as the one disclosed in co-pending U.S. provisional No. 61/526,833 or PCT/US12/052163 (Examples 16 and 17), or derived from a strain of *Trichoderma*, such as a strain of *Trichoderma reesei*, such as the mature polypeptide of SEQ ID NO: 58 in WO 2011/057140.

Paragraph 7. The enzyme composition of any of paragraphs 1-6, wherein the cellulolytic preparation comprises a cellobiohydrolase I (CBH I), such as one derived from a strain of the genus *Aspergillus*, such as a strain of *Aspergillus fumigatus*, such as the Cel7a CBHI disclosed in SEQ ID NO: 2 in WO 2011/057140, or a strain of the genus *Trichoderma*, such as a strain of *Trichoderma reesei*.

Paragraph 8. The enzyme composition of any of paragraphs 1-7, wherein the cellulolytic preparation comprises a cellobiohydrolase II (CBH II, such as one derived from a strain of the genus *Aspergillus*, such as a strain of *Aspergillus fumigates*; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

Paragraph 9. The enzyme composition of any of paragraphs 1-8, wherein the acetylxylan esterase (AXE) is derived from a strain of the genus *Thielavia*, such as a strain of *Thielavia terrestris*, such as one disclosed in WO 2009/042846 as SEQ ID NO: 2 or SEQ ID NO: 1 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2009/042846 or SEQ ID NO: 1 herein.

Paragraph 10. The enzyme composition of any of paragraphs 1-8, wherein the acetylxylan esterase (AXE) is derived from a strain of the genus *Aspergillus*, such as a strain of *Aspergillus aculaetus*, such as one disclosed in WO 2010/108918 as SEQ ID NO: 2 or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2010/108918.

Paragraph 11. The enzyme composition of any of paragraphs 1-8, wherein the acetylxylan esterase (AXE) is derived from a strain of the genus *Aspergillus*, such as a strain of *Aspergillus aculaetus*, such as *Aspergillus aculeatus* CBS 101.43, such as the one disclosed in WO 1995/002689 as SEQ ID NO: 5 or an acetylxylan esterase having at least 80%, such as at least 85%, such as at least 90%, preferably 95%, such as at least 96%, such as 97%, such as at least 98%, such as at least 99% identity to SEQ ID NO: 5 in WO 1995/002689.

Paragraph 12. The enzyme composition of any of paragraphs 1-8, wherein the acetylxylan esterase (AXE) is derived from a strain of the genus *Humicola* such as a strain of *Humicola insolens*, such as one disclosed in WO 2009/073709 as SEQ ID NO: 2 or as SEQ ID NO: 3 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2009/073709 or as SEQ ID NO: 3 herein.

Paragraph 13. The enzyme composition of any of paragraphs 1-12, wherein the cellulolytic preparation comprises a GH61 polypeptide having cellulolytic enhancing activity and a beta-glucosidase.

Paragraph 14. The enzyme composition of any of paragraphs 1-12, wherein the cellulolytic preparation comprises a GH61 polypeptide having cellulolytic enhancing activity, a beta-glucosidase, and a xylanase.

Paragraph 15. The enzyme composition of any of paragraphs 1-12, wherein the cellulolytic preparation comprises a GH61 polypeptide having cellulolytic enhancing activity, a beta-glucosidase, a xylanase and a beta-xylosidase.

Paragraph 16. The enzyme composition of any of paragraphs 1-12, wherein the cellulolytic preparation comprises a GH61 polypeptide having cellulolytic enhancing activity, a beta-glucosidase, a xylanase, a beta-xylosidase, and a CBHI.

Paragraph 17. The enzyme composition of any of paragraphs 1-12, wherein the cellulolytic preparation comprises a GH61 polypeptide having cellulolytic enhancing activity, a beta-glucosidase, a xylanase, a beta-xylosidase, a CBHI and a CBHII.

Paragraph 18. The enzyme composition of any of paragraphs 1-17, wherein the cellulolytic preparation is a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus oryzae* beta-glucosidase fusion protein (WO 2008/057637), and *Aspergillus aculeatus* xylanase (Xyl II in WO 94/21785).

Paragraph 19. The enzyme composition of any of paragraphs 1-17, wherein the cellulolytic preparation is a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785).

Paragraph 20. The enzyme composition of any of paragraphs 1-17, wherein the cellulolytic preparation is a *Trichoderma reesei* cellulolytic preparation further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785) and the acetylxylan esterase (AXE) is the one derived from *Thielavia terrestris* disclosed in WO 2009/042846 as SEQ ID NO: 2 or SEQ ID NO: 1 herein or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846 SEQ ID NO: 1 herein.

Paragraph 21. The enzyme composition of any of paragraphs 1-17, wherein the cellulolytic preparation is a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) and *Aspergillus fumigatus* xylanase (Xyl III in WO 2006/078256) and the acetylxylan esterase (AXE) is the one derived from *Thielavia terrestris* disclosed in WO 2009/042846 as SEQ ID NO: 2 or SEQ ID NO: 1 or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846 SEQ ID NO: 1.

Paragraph 22. The enzyme composition of any of paragraphs 1-21, wherein the ratio between cellulolytic preparation and acetylxylan esterase (AXE) is in the range between 500:1 and 100:1, such as between 50:1 and 2:1, such as around 4:1.

Paragraph 23. A method of hydrolyzing acetylated cellulosic material, comprising subjecting the acetylated cellulosic material to a cellulolytic preparation and an acetylxylan esterase (AXE).

Paragraph 24. The method of paragraph 23, wherein acetylated cellulosic material is pretreated cellulosic material.

Paragraph 25. The method of paragraph 23 or 24, wherein the cellulosic material is plant material chips, plant stem segments and/or whole plant stems.

Paragraph 26. The method of paragraph 25, wherein cellulosic material is selected from the group comprising arundo, bagasse, bamboo, corn cob, corn fiber, corn stover, miscanthus, orange peel, rice straw, switchgrass, wheat straw.

Paragraph 27. The method of paragraph 26, wherein the source of the cellulosic material is corn stover, corn cobs, and/or wheat straw.

Paragraph 28. The method of any of paragraphs 24-27, wherein the pretreating cellulosic material is pretreated by chemical pretreatment, a physical pretreatment, or a chemical pretreatment and a physical pretreatment.

Paragraph 29. The method of any of paragraphs 24-28, wherein the cellulosic material is thermomechamically pulped plant material.

Paragraph 30. The method of any of paragraphs 24-29, wherein the acetylated cellulosic material is thermomechanically pulped plant material, such as acetylated corn stover pulp.

Paragraph 31. The method of any of paragraphs 24-30, wherein pretreating the cellulosic material includes pretreatment with an acid.

Paragraph 32. The method of any of paragraphs 24-31, wherein the acetylated cellulosic material has been prepared by pretreating cellulosic material at high temperature, high pressure with an acid.

Paragraph 33. The method of paragraph 31 or 32, wherein acid pretreatment is carried out using acetic acid.

Paragraph 34. The method of any of paragraphs 24-33, wherein the acetylated cellulosic material has been prepared by pretreating cellulosic material using organosolv pretreatement, such as Acetosolv and Acetocell processes.

Paragraph 35. The method of any of paragraphs 24-34, wherein the soluble fractions containing sugars, acid and solubilized lignin is removed from the acetylated cellulosic material after pretreatment.

Paragraph 36. The method of any of paragraphs 24-35, wherein hydrolysis is carried out at a temperature between 20-70° C., such as 30-60° C., preferably 45-55° C. at a pH in the range 4-6, such as 4.5-5.5.

Paragraph 37. The method of any of paragraph 24-36, wherein the cellulosic material is present at 1-20 (w/w) % of TS, such as 2-10 (w/w) % TS, such as around 5 (w/w) % TS.

Paragraph 38. The method of any of paragraphs 24-37, wherein the hydrolysis is carried out for 1-20 days, preferably between from 5-15 days.

Paragraph 39. The method of any of paragraphs 24-38, wherein the cellulolytic preparation is derived from *Trichoderma reesei, Humicola insolens* or *Chrysosporium lucknowense*.

Paragraph 40. The method of any of paragraphs 24-39, wherein the cellulolytic preparation comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or an *Aspergillus fumigatus* beta-glucosidase variant disclosed in co-pending U.S. provisional application No. 61/388,997 or WO 2012/044915 with the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

Paragraph 41. The method of any of paragraphs 24-40, wherein the cellulolytic preparation comprises a GH61 polypeptide having cellulolytic enhancing activity, such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigates*, such as the one as described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397.

Paragraph 42. The method of any of paragraphs 24-41, wherein the cellulolytic preparation comprises a xylanase, preferably a GH10 xylanase, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

Paragraph 43. The method of any of paragraphs 24-41, wherein the cellulolytic preparation comprises a beta-xylosidase, such as one derived from a strain of the genus *Aspergillus*, such as a strain of *Aspergillus fumigatus*, such as the one disclosed in co-pending U.S. provisional No. 61/526,833 or PCT/US12/052163, or derived from a strain of *Trichoderma*, such as a strain of *Trichoderma reesei*, such as the mature polypeptide of SEQ 10 NO: 58 in WO 2011/057140.

Paragraph 44. The method of any of paragraphs 24-42, wherein the acetylxylan esterase (AXE) is derived from a strain of the genus *Thielavia*, such as a strain of *Thielavia terrestris*, such as one disclosed in WO 2009/042846 as SEQ ID NO: 2 or SEQ ID NO: 1 herein or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846.

Paragraph 45. The method of any of paragraphs 24-43, wherein the acetylxylan esterase (AXE) is derived from a strain of the genus *Aspergillus*, such as a strain of *Aspergillus aculaetus*, such as one disclosed in WO 2010/108918 as SEQ ID NO: 2 or SE ID NO: 2 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2010/108918 or SEQ ID NO: 2 herein.

Paragraph 46. The method of any of paragraphs 24-43, wherein the acetylxylan esterase (AXE) is derived from a strain of the genus *Aspergillus*, such as a strain of *Aspergillus aculaetus*, such as *Aspergillus aculeatus* CBS 101.43, such as the one disclosed in WO 1995/002689 as SEQ ID NO: 5 or an acetylxylan esterase having at least 80%, such as at least 85%, such as at least 90%, preferably Paragraph 47. The method of any of paragraphs 24-43, wherein the acetylxylan esterase (AXE) is derived from a strain of the genus *Humicola* such as a strain of *Humicola insolens*, such as one disclosed in WO 2009/073709 as SEQ ID NO: 2 or as SEQ ID NO: 3 herein or an acetylxylan esterase having at least 80%, such as at least 85%, such as at least 90%, preferably 95%, such as at least 96%, such as 97%, such as at least 98%, such as at least 99% identity to SEQ ID NO: 2 in WO 2009/073709 or as SEQ ID NO: 3 herein.

Paragraph 48. The method of any of paragraphs 24-47, wherein the cellulolytic preparation comprises a cellobiohydrolase I (CBHI), such as one derived from a strain of the genus *Aspergillus*, such as a strain of *Aspergillus fumigatus*, or a strain of the genus *Trichoderma*, such as a strain of *Trichoderma reesei*.

Paragraph 49. The method of any of paragraphs 24-48, wherein the cellulolytic preparation comprises a cellobiohydrolase II (CBHII), such as one derived from *Aspergillus fumigates*; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

Paragraph 50. The method of any of paragraphs 24-49, wherein the cellulolytic preparation comprises a GH61 polypeptide having cellulolytic enhancing activity and a beta-glucanase.

Paragraph 51. The method of any of paragraphs 24-49, wherein the cellulolytic preparation comprises a GH61 polypeptide having cellulolytic enhancing activity, a beta-glucanase, and a xylanase.

Paragraph 52. The method of any of paragraphs 24-49, wherein the cellulolytic preparation comprises a GH61 polypeptide having cellulolytic enhancing activity, a beta-glucanase, a xylanase and a beta-xylosidase.

Paragraph 53. The method of any of paragraphs 24-49, wherein the cellulolytic preparation comprises a GH61 polypeptide having cellulolytic enhancing activity, a beta-glucanase, a xylanase, a beta-xylosidase, and a CBHI.

Paragraph 54. The method of any of paragraphs 24-49, wherein the cellulolytic preparation comprises a GH61 polypeptide having cellulolytic enhancing activity, a beta-glucanase, a xylanase, a beta-xylosidase, a CBHI and a CBHII.

Paragraph 55. The method of any of paragraphs 24-54, wherein the cellulolytic preparation is a *Trichoderma reesei* cellulolytic preparation, further comprising *Thermoascus aurantiacus* GH61A polypeptide having cellulolytic enhancing activity (SEQ ID NO: 1 and SEQ ID NO: 2 in WO 2005/074656), *Aspergillus oryzae* beta-glucosidase fusion protein (WO 2008/057637), and *Aspergillus aculeatus* xylanase (Xyl II in WO 94/21785).

Paragraph 56. The method of any of paragraphs 24-55, wherein the cellulolytic preparation is a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785).

Paragraph 57. The method of any of paragraphs 24-56, wherein the cellulolytic preparation is a *Trichoderma reesei* cellulolytic preparation, further comprising *Penicillium emersonii* GH61A polypeptide having cellulolytic enhancing activity (SEQ ID NO: 2 in WO 2011/04139, *Aspergillus fumigatus* beta-glucosidase variant (disclosed in U.S. provisional application No. 61/388,997 or WO 2012/044915 with the following substitutions: F100D, S283G, N456E, F512Y and *Aspergillus fumigatus* xylanase (Xyl III disclosed in WO 2006/078256) and beta-xylosidase derived from a strain of *Aspergillus fumigatus*.

Paragraph 58. The method of any of paragraphs 24-57, wherein the cellulolytic preparation is added in amounts of about 0.01 to about 50.0 mg, e.g., about 1 to about 25 mg, such as about 2-10 mg, such as about 4 to about 8 mg protein per g/DS of the cellulosic material.

Paragraph 59. The method of any of paragraphs 24-58, wherein the acetylxylan esterase (AXE) is used in amounts of 0.01 to about 10 mg, such as 0.05 to about 5 mg, such as 0.1 to about 4 mg enzyme protein per g/DS of the cellulosic material.

Paragraph 60. The method of any of paragraphs 24-59, wherein the ratio between cellulolytic preparation and acetylxylan esterase (AXE) is in the range in a ratio of between 500:1 and 1:1, such as between 50:1 and 2:1, such as about 4:1.

Paragraph 61. The method of any of paragraphs 24-60, wherein the cellulolytic preparation is a *Trichoderma reesei* cellulolytic preparation further comprising *Thermoascus aurantiacus* GH61A polypeptide having cellulolytic enhancing activity (SEQ ID NO: 1 and SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785), further comprising and the acetylxylan esterase (AXE) derived from *Thielavia terrestris* disclosed in WO 2009/042846 as SEQ ID NO: 2 or SEQ ID NO: 1 herein or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846 or SEQ ID NO: 1 herein.

Paragraph 62. The method of any of paragraphs 24-61, wherein the cellulolytic preparation is a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase variant (disclosed in co-pending U.S. provisional application No. 61/388,997 or WO 2012/044915 with the following substitutions: F100D, S283G, N456E, F512Y, *Aspergillus fumigatus* xylanase (Xyl III in WO 2006/078256), further comprising the acetylxylan esterase (AXE) derived from *Thielavia terrestris* disclosed in WO 2009/042846 as SEQ ID NO: 2 or SEQ ID NO: 1 herein or an acetylxylan esterase having at least 80%, such as at least 85%, such as at least 90%, preferably at least 95%, such as at least 96%, such as at least 97%, such as at least 98%, such as at least 99% identity to SEQ ID NO: 2 in WO 2009/042846 or SEQ ID NO: 1 herein.

Paragraph 63. A process of producing a fermentation product from acetylated cellulosic material, comprising:
 (a) hydrolyzing said acetylated cellulosic material by subjecting the material to an enzyme composition according to any of paragraphs 1-23 or according to any one of the hydrolysis method paragraphs in any of paragraphs 24-62;
 (b) fermenting using a fermenting organism; and
 (c) optionally recovering the fermentation product.

Paragraph 64. The process of paragraph 63, wherein the fermentation product is ethanol.

Paragraph 65. The process of paragraph 63 or 64, wherein the fermenting organism is a yeast, such as strain of the genus Saccharomyces, such as a strain of Saccharomyce cerevisie.

Paragraph 66. The process of any of paragraphs 63-65, wherein the cellulosic material is corn stover pulp.

Materials & Methods
Enzymes:
  Trichoderma reesei cellulolytic preparation
  Thermoascus aurantiacus GH61 polypeptide having cellulolytic enhancing activity described in WO 2005/074656 as SEQ ID NO: 2.
  Aspergillus fumigatus beta-glucosidase disclosed in WO 2005/047499.
  Aspergillus fumigatus beta-glucosidase variant disclosed in WO 2012/044915 with the following substitutions F100D, S283G, N456E, F512Y.
  Aspergillus aculeatus xylanase disclosed in WO 94/21785 as SEQ ID NO: 5 (Xyl II).
  Thielavia terrestris acetylxylan esterase disclosed in WO 2009/042846 as SEQ ID NO: 2 or SEQ ID NO: 1 herein. (P6GE)
  Aspergillus aculeatus acetyl xylan esterase disclosed in WO 2010/108918 as SEQ ID NO: 2 or SEQ ID NO: 2 herein. (NP002824)
  Aspergillus fumigatus Cel7A CBH1 disclosed in SEQ ID NO: 2 in WO 2011/057140.
  Aspergillus fumigatus CBH2 available from Novozymes A/S.
  Aspergillus fumigatus beta-xylosidase disclosed in co-pending U.S. provisional No. 61/526,833 or PCT/US12/052163 (Examples 16 and 17).

Acetylated Cellulosic Material:
  Acetylated corn stover pulp containing about 75% cellulose and 11% xylan was obtained from Archer Daniels Midland (ADM), USA.

Methods
Determination of Acetyl Group in Cellulosic Material
  Carbohydrates and acetate groups can be measured as per NREL methods (see A. Sluiter et al "Determination of Structural Carbohydrates and Lignin in Biomass, pp 15-18—NREL/TP-510-42618, Revised July 2011) and nrel.gov/biomass/pdfs/42618.pdf.

EXAMPLES

Example 1

Improved Cellulose and Xylan Conversion Using AXE

Acetylated corn stover pulp containing about 75% cellulose and 11% xylan was used. The degree of acetylation based on overall carbohydrates was measured to be around 8% (1 acetyl group per 12.5 sugar units). Corn stover pulp was prepared by pretreating corn stover at high temperature and pressure using acetic acid. The resulting slurry was put through a solid/liquid separator (pressure filtration) to remove soluble fractions containing sugars, acetic acid and solubilized lignin. The insoluble substrate (acetylated pulp) was washed with tap water to a pH above 5.0 and was subjected to enzymatic hydrolysis in a 24 well (5 mL) polypropylene cell growth plates (Whatman Uniplate) in quadruplicates at a 5 g hydrolysis scale, 2.5% solids, 50 mM citrate buffer, pH of 5.1 and 50° C. for 11 days using
  i) Trichoderma reesei cellulolytic preparation, Thermoascus aurantiacus GH61A polypeptide having cellulolytic enhancing activity (described in WO 2005/074656 as SEQ ID NO: 2), Aspergillus fumigatus beta-glucosidase (WO 2005/047499), and Aspergillus aculeatus xylanase (disclosed in WO 94/21785 as SEQ ID NO: 5 (referred to as Xyl II) at dosage of 6 mg protein/g cellulose:
  ii) Trichoderma reesei cellulolytic preparation, Thermoascus aurantiacus GH61A polypeptide having cellulolytic enhancing activity (described in WO 2005/074656 as SEQ ID NO: 2), Aspergillus fumigatus beta-glucosidase (WO 2005/047499), and Aspergillus aculeatus xylanase (disclosed in WO 94/21785 as SEQ ID NO: 5 (Xyl II)) at dosage of 4.8 mg protein/g cellulose;
  iii) Cellulolytic preparation as described above in ii) at 4.8 mg protein/g cellulose along with 1.2 mg protein/g cellulose of Aspergillus aculeatus acetyl xylan esterase I (disclosed in WO 2010/108918 as SEQ ID NO: 2 (NP000409));
  Cellulolytic preparation as described above in ii) at 4.8 mg protein/g cellulose along with 1.2 mg/g cellulose of Thielavia terrestris acetyl xylan esterase (disclosed in WO 2009/042846 as SEQ ID NO: 2 (P6GE);

The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. Glucose and xylose yields were calculated as % of theoretical based on initial cellulose and xylan input and concentrations of glucose and xylose obtained after enzyme hydrolysis.

Figure 2:
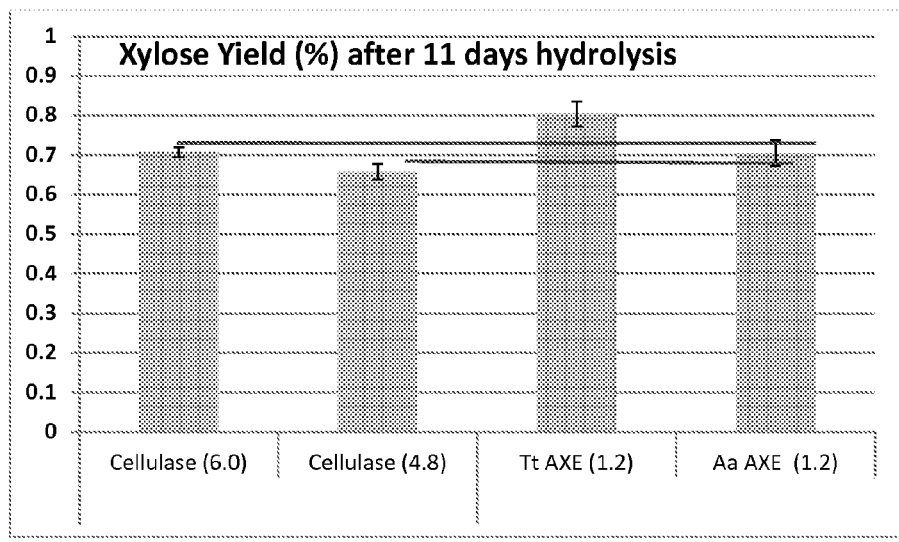
FIG. 2 shows the xylose yield (%) after 11 days hydrolysis.

The results obtained after 11 day hydrolysis are shown in Table 1 as well as in FIG. 1 and FIG. 2. The acetylxylan esterases showed activity toward improving glucose yield and in particular Thielavia terrestris acetyl xylan esterase showed significant benefit in improving cellulose conversion to glucose (FIG. 1). It is also seen that several acetyl xylan esterases and in particular Thielavia terrestris could improve xylose yield in addition to glucose yield from pretreated corn stover.

TABLE 1

11 day hydrolysis results

| | Protein (mg) | Avg. Glucose Yield (%) | Std Dev (Glucose) | Avg. Xylose Yield (%) | Std Dev (Xylose) |
|---|---|---|---|---|---|
| plus cellulase (4.8) | Cellulase (6.0) | 56 | 1.6 | 71 | 1.2 |
| | Cellulase (4.8) | 45 | 0.7 | 66 | 2.0 |
| | Tt AXE (1.2) | 67 | 2.5 | 80 | 3.2 |
| | Aa AXE (1.2) | 50 | 2.4 | 70 | 3.3 |

Example 2

Figure 3:
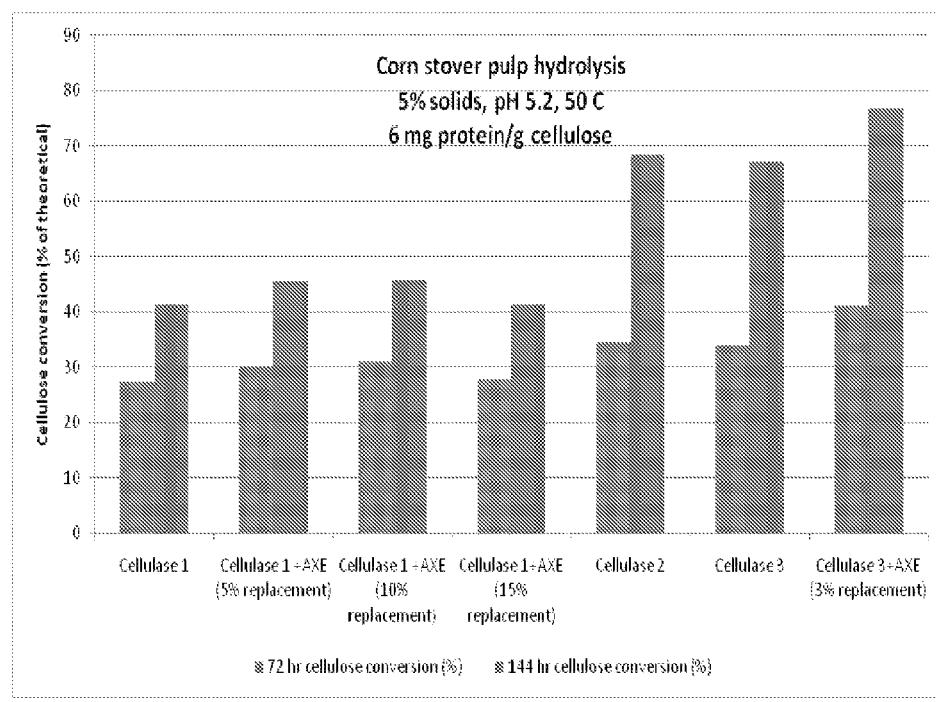
FIG. 3 shows the results from pretreated acetylated corn stover pulp (5% solids, pH 5.2, 50° C., 6 mg protein/g cellulose).

Improved Cellulose Conversion of Acetylated Corn Stover Pulp Using Cellulolytic Preparations Further Comprising Thilavia terrestris AXE The acetylated corn stover pulp containing about 75% cellulose and 11% xylan was used. The degree of acetylation based on overall carbohydrates was measured to be around 8% (1 acetyl group per 12.5 sugar units). Corn stover pulp was prepared by pretreating corn stover at high temperature and pressure using acetic acid. The resulting slurry was put through a S/L separator (pressure filtration) to remove soluble fractions containing sugars, acetic acid and solubilized lignin. The insoluble substrate (acetylated pulp) was washed with tap water to a pH above 5.0 and was subjected to enzymatic hydrolysis in a rotisserie incubator in duplicates at a 20 g hydrolysis scale, 5% solids, 50 mM citrate buffer, pH of 5.0 and 50° C. for 3 and 6 days with same amounts of total protein per g of cellulose using i) *Trichoderma reesei* cellulolytic preparation, *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499), and *Aspergillus aculeatus* xylanase (Xyl II disclosed in WO 94/21785) at dosage of 6 mg protein/g cellulose (cellulase 1 in FIG. 3);

ii) Cellulolytic preparation as described above in i) at 5.7 mg protein/g cellulose along with 0.3 mg protein/g cellulose of *Thielavia terrestris* acetyl xylan esterase (disclosed in WO 2009/042846 as SEQ ID NO: 2 (P6GE) at 5% replacement level) (cellulase 1+AXE (5% replacement) in FIG. 3);

iii) Cellulolytic preparation as described above in i) at 5.4 mg protein/g cellulose along with 0.6 mg protein/g cellulose of *Thielavia terrestris* acetylxylan esterase (disclosed in WO 2009/042846 as SEQ ID NO: 2 (P6GE) at 10% replacement level) (cellulase 1+AXE (10% replacement) in FIG. 3);

iv) Cellulolytic preparation as described above in i) at 5.1 mg protein/g cellulose along with 0.9 mg protein/g cellulose of *Thielavia terrestris* acetylxylan esterase (disclosed in WO 2009/042846 as SEQ ID NO: 2 (P6GE) at 15% replacement level) (cellulase 1+AXE (15% replacement) in FIG. 3);

v) *Trichoderma reesei* cellulolytic preparation with *Aspergillus fumigatus* Cel7A CBH I (disclosed in SEQ ID NO: 2 in WO 2011/057140 and CBH II, *Thermoascus aurantiacus* GH61A polypeptide having cellulolytic enhancing activity (SEQ ID NO: 2 in WO 2005/074656), *Aspergillus fumigatus* beta-glucosidase variant with the following substitutions: F100D, S283G, N456E, F512Y (WO 2012/044915), and *Aspergillus fumigatus* xylanase (Xyl III in WO 2006/078256) at dosage of 6 mg protein/g cellulose (experimental cellulase 2 in FIG. 3);

vi) *Trichoderma reesei* cellulolytic preparation with *Aspergillus fumigatus* CBH I and CBH II, *Thermoascus aurantiacus* GH61 polypeptide having cellulolytic enhancing activity (SEQ ID NO: 2 in WO 2005/074656), *Aspergillus fumigatus* beta-glucosidase variant disclosed in co-pending U.S. provisional application No. 61/388,997), *Aspergillus fumigatus* xylanase (Xyl III in WO 2006/078256) and *Aspergillus fumigatus* beta-xylosidase (disclosed in co-pending U.S. provisional No. 61/526,833 or PCT/US12/052163 (Examples 16 and 17) at dosage of 6 mg protein/g cellulose (cellulase 3 in FIG. 3);

vii) Cellulase as described above in vi) at 5.82 mg protein/g cellulose along with 0.18 mg protein/g cellulose of *Thielavia terrestris* acetylxylan esterase (disclosed in WO 2009/042846 as SEQ ID NO: 2 (P6GE) at 3% replacement level) (cellulase 3+AXE (3% replacement) in FIG. 3).

The sugar concentrations of samples diluted in 0.005 M $H_2SO_4$ were measured using a 4.6×250 mm AMINEX® HPX-87P column (Bio-Rad Laboratories, Inc., Hercules, Calif., USA) by elution with MilliQ-$H_2O$ at 80° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. Cellulose conversion was calculated as % of theoretical based on initial cellulose and xylan input and concentrations of glucose and xylose obtained after enzyme hydrolysis.

The results obtained after 72 hrs and 144 hrs hydrolysis are shown in Table 2 and FIG. 3. The results show that cellulases 2 and 3 showed substantial improvement in cellulose conversion over cellulase 1 performance at the same protein dose of 6 mg per g of cellulose. Further a 3% replacement of experimental cellulase 3 protein by *Thielavia terrestris* acetylxylan esterase boosted the cellulose conversion further to 76.7% from about 67.2%.

TABLE 2

72 hr and 144 hr cellulose conversion

|  | 72 hr cellulose conversion (%) | 144 hr cellulose conversion (%) |
| --- | --- | --- |
| Cellulase 1 | 27.3 | 41.4 |
| Cellulase 1 + AXE (5% replacement) | 29.9 | 45.5 |
| Cellulase 1 + AXE (10% replacement) | 31 | 45.7 |
| Cellulase 1 + AXE (15% replacement) | 27.8 | 41.5 |
| Cellulase 2 | 34.5 | 68.4 |
| Cellulase 3 | 33.9 | 67.2 |
| Cellulase 3 + AXE (3% replacement) | 41.1 | 76.7 |

The invention claimed is:

1. A method of hydrolyzing acetylated acid-pretreated cellulosic material, comprising subjecting the acetylated cellulosic material to a cellulolytic preparation and an acetylxylan esterase (AXE),
wherein the acetylxylan esterase (AXE) is obtained from a strain of *Aspergillus aculaetus* and has at least 80% sequence identity to SEQ ID NO: 2.

2. The method of claim 1, wherein the acetylated acid-pretreated cellulosic material is thermomechanically pulped plant material.

3. The method of claim 1, wherein the cellulolytic preparation is a *Trichoderma reesei* cellulolytic preparation, further comprising *Penicillium emersonii* GH61A polypeptide having cellulolytic enhancing activity, *Aspergillus fumigatus* beta-glucosidase variant and *Aspergillus fumigatus* beta-xylosidase.

4. The method of claim 1, wherein the ratio between cellulolytic preparation and acetylxylan esterase (AXE) is in the range in a ratio of between 500:1 and 1:1, between 50:1 and 2:1, or about 4:1.

5. A process of producing a fermentation product from acetylated acid-pretreated cellulosic material, comprising:

(a) hydrolyzing said acetylated acid-pretreated cellulosic material by subjecting the material to an enzyme composition comprising a cellulolytic preparation and an acetylxylan esterase (AXE),
wherein the acetylxylan esterase (AXE) is obtained from a strain of *Aspergillus aculaetus* and has at least 80% sequence identity to SEQ ID NO: 2;

(b) fermenting using a fermenting organism; and (c) optionally recovering the fermentation product.

6. The process of claim 5, wherein the fermentation product is ethanol.

7. The process of claim 5, wherein the acetylated acid-pretreated cellulosic material is corn stover pulp.

8. The method of claim 2, wherein the thermomechanically pulped plant material is acetylated corn stover pulp.

9. The method of claim 1, wherein the acetylated acid-pretreated cellulosic material has a degree of acetylation of the cellulosic material of about 5-10%.

10. The method of claim 5, wherein the acetylated acid-pretreated cellulosic material has a degree of acetylation of the cellulosic material of about 5-10%.

11. The method of claim 1, wherein the acetylxylan esterase has at least 85% sequence identity to SEQ ID NO: 2.

12. The method of claim 1, wherein the acetylxylan esterase has at least 90% sequence identity to SEQ ID NO: 2.

13. The method of claim 1, wherein the acetylxylan esterase has at least 95% sequence identity to SEQ ID NO: 2.

14. The method of claim 1, wherein the acetylxylan esterase has at least 96% sequence identity to SEQ ID NO: 2.

15. The method of claim 1, wherein the acetylxylan esterase has at least 97% sequence identity to SEQ ID NO: 2.

16. The method of claim 1, wherein the acetylxylan esterase has at least 98% sequence identity to SEQ ID NO: 2.

17. The method of claim 1, wherein the acetylxylan esterase has at least 99% sequence identity to SEQ ID NO: 2.

18. The method of claim 5, wherein the acetylxylan esterase has at least 85% sequence identity to SEQ ID NO: 2.

19. The method of claim 5, wherein the acetylxylan esterase has at least 90% sequence identity to SEQ ID NO: 2.

20. The method of claim 5, wherein the acetylxylan esterase has at least 95% sequence identity to SEQ ID NO: 2.

21. The method of claim 5, wherein the acetylxylan esterase has at least 96% sequence identity to SEQ ID NO: 2.

22. The method of claim 5, wherein the acetylxylan esterase has at least 97% sequence identity to SEQ ID NO: 2.

23. The method of claim 5, wherein the acetylxylan esterase has at least 98% sequence identity to SEQ ID NO: 2.

24. The method of claim 5, wherein the acetylxylan esterase has at least 99% sequence identity to SEQ ID NO: 2.

* * * * *